(12) United States Patent
Sugiyama et al.

(10) Patent No.: US 7,566,330 B2
(45) Date of Patent: Jul. 28, 2009

(54) DISPOSABLE DIAPER

(75) Inventors: Katsuhiko Sugiyama, Tokyo (JP);
Kahori Suzuki, Tokyo (JP); Izumi Tashiro, Tokyo (JP)

(73) Assignees: Oji Nepia Co., Ltd., Chuo-Ku (JP); Oji Paper Co., Ltd., Chuo-Ku (JP)

( * ) Notice: Subject to any disclaimer, the term of this patent is extended or adjusted under 35 U.S.C. 154(b) by 0 days.

(21) Appl. No.: 11/545,712

(22) Filed: Oct. 10, 2006

(65) Prior Publication Data
US 2007/0088310 A1   Apr. 19, 2007

(30) Foreign Application Priority Data
Oct. 14, 2005  (JP)  ............. 2005-300394
Aug. 14, 2006  (JP)  ............. 2006-221025

(51) Int. Cl.
*A61F 13/15* (2006.01)
(52) U.S. Cl. ............. 604/385.28; 604/385.26; 604/385.24; 604/385.29; 604/385.3; 604/385.09; 604/385.101
(58) Field of Classification Search ............ 604/385.24, 604/385.26, 385.28, 385.29, 385.3, 385.09, 604/385.101
See application file for complete search history.

(56) References Cited

U.S. PATENT DOCUMENTS

| | | | |
|---|---|---|---|
| 4,462,116 A | 7/1984 | Sanzone et al. | 2/170 |
| 4,591,356 A | 5/1986 | Christie | 604/179 |
| 5,140,996 A | 8/1992 | Sommers et al. | 128/849 |
| 5,549,567 A | 8/1996 | Wolman | 604/179 |
| 5,858,054 A | 1/1999 | Rosen | 66/202 |
| 6,155,263 A | 12/2000 | Weaver | 128/878 |
| 6,192,717 B1 | 2/2001 | Rabinowicz | 66/177 |
| 6,243,867 B1 | 6/2001 | Faison | 2/16 |
| 6,405,381 B1 | 6/2002 | Bowman, Jr. | 2/170 |
| 6,571,395 B1 | 6/2003 | Korkor | 2/45 |
| 2004/0039363 A1 | 2/2004 | Sugiyama et al. | |

FOREIGN PATENT DOCUMENTS

| | | |
|---|---|---|
| GB | 2 268 073 | 1/1994 |
| JP | 2559050 | 9/1997 |
| JP | 09-510384 | 10/1997 |
| JP | 2002-011044 | 1/2001 |
| WO | 95/25493 | 9/1995 |

OTHER PUBLICATIONS

Kazuya Yamamoto, Hifu Rinsho (Clinical Dermatology) 1988, vol. 30, pp. 949-956.

*Primary Examiner*—Jacqueline F. Stephens
(74) *Attorney, Agent, or Firm*—Burr & Brown (57) ABSTRACT

A disposable diaper is provided which includes an absorber, a top sheet which is at least partially formed of a liquid permeable material disposed to cover an upper surface of the absorber, a back sheet formed of a liquid impermeable material disposed to cover a lower surface of the absorber, a skin contact sheet disposed above the top sheet and having a stool passing opening capable of passing a stool therethrough formed therein, and a urine/stool separation wall formed of a breathable water repellent sheet disposed in a space between the skin contact sheet and the top sheet so that the space is separated into a front body part side space and a back body part side space.

8 Claims, 9 Drawing Sheets

DISPOSABLE DIAPER

BACKGROUND OF THE INVENTION

Field of the Invention

In recent years, as a diaper for an infant or an elder or disabled person, there has been widely used a disposable diaper which includes an absorber, a top sheet disposed to cover the upper surface of the absorber and at least partially formed of a liquid permeable material, and a back sheet disposed to cover the lower surface of the absorber and formed of a liquid impermeable material. This disposable diaper is used in such a manner that a surface of the top sheet is applied to contact the skin of a wearer of the disposable diaper. Thereby, the urine discharged by the wearer penetrates through the top sheet and is absorbed and retained by the absorber. Further, the back sheet having good leakage preventing performance prevents the leakage of the excrement to the outside of the diaper.

In the disposable diaper of the above-described structure, however, the urine penetrates through the top sheet, but most of the stool does not penetrate through the top sheet and thus remains thereon. The stool remaining on the top sheet adheres to the crotch part or the buttocks of the wearer. This requires troublesome wiping work which increases the burden of child rearing or nursing care, and also causes skin trouble to the wearer. Such phenomenon becomes more prominent when the stool discharged by the wearer is an unformed stool.

In view of this, another type of disposable diaper has been proposed in which another sheet member (hereinafter referred to as a "skin contact sheet" in the present specification) is disposed above the top sheet (see Paragraph 0010 and FIG. 2 of Japanese Registered Utility Model No. 2559050, and Paragraphs 0044 to 0046 and FIGS. 10 to 12 of Japanese Unexamined Patent Application Publication No. 2002-11044, for example). These disposable diapers are structured such that the skin contact sheet is formed with an opening capable of passing the stool therethrough (i.e., a stool passing opening) for causing the stool discharged by the wearer to drop on the top sheet through the stool passing opening.

According to the above-described disposable diaper, the skin contact sheet first contacts the skin of the wearer. Thus, the top sheet disposed under the skin contact sheet does not easily come into direct contact with the skin of the wearer. That is, the skin of the wearer is separated from the top sheet. This also means that a shielding layer, i.e., the skin contact sheet, intervenes between the top sheet and the skin of the wearer. Therefore, even if the stool remains on the top sheet, the effect of substantially decreasing the chance of direct contact between the stool and the skin of the wearer can be expected.

If the urine and the stool are mixed, ammonia is generated and alkalinizes the surrounding environment. Then, an enzyme included in the stool is strongly activated in an alkaline atmosphere, and the enzyme and ammonia inflame a weakened part of the skin. Thereby, the diaper rash occurs. This mechanism is reported by Kazuya Yamamoto in Hifu Rinsho (Clinical Dermatology) 1988, vol. 30, pp 949-956.

In view of this, in the disposable diaper discussed in Japanese Unexamined Patent Application Publication No. 2002-11044, an improvement has been made in that a dam is formed to a crotch part of a diaper with a top sheet or an absorber, or a pocket part is formed by thinning the thickness of the absorber from the crotch part to a back body part side.

In the disposable diaper discussed in the Japanese Unexamined Patent Application Publication No. 2002-11044, by the dam formed in the crotch part of the disposable diaper, movement of urine to the back body part side and movement of stool to a front body part side is prevented. Further, by the pocket part formed from the crotch part to the back body part side, movement of the stool to the front body part side is prevented. Accordingly, the urine and stool discharged by a wearer hardly mix with each other, the effect of reducing diaper rash can be expected.

However, in the disposable diaper discussed in the Japanese Unexamined Patent Application Publication No. 2002-11044, although the mixture of the urine and stool can be prevented to some degree, it has not progressed to the level of definitely separating the urine and stool discharged by the wearer and absorbing and retaining the separated urine and stool, and sometimes the urine and the stool mixes each other. That is, the disposable diaper is not satisfactory enough in definitely separating the urine and stool discharged by the wearer and absorbing and retaining the separated urine and stool, and thus is still open to improvement.

The present inventors conducted a keen examination to improve the above-described conventional techniques and obtained a finding that the disposable diaper discussed in the Japanese Unexamined Patent Application Publication No. 2002-11044 has a space above the formed dam and therefore, the stool can move over the dam to the front body part side. Further, generally, because the dam is formed with a top sheet made of a liquid permeable sheet (hydrophilic sheet), the urine can penetrate the dam to the back body part side. Accordingly, in the disposable diaper, the separation effect of the urine and stool tends to be insufficiently. Then, to solve the above-described disadvantages, the present inventors has been made with the idea of forming a urine/stool separation wall made of a breathable water repellent sheet in the space between the skin contact sheet and the top sheet and separating the space into a front body part side and a back body part side. Specifically, the present invention provides the following disposable diaper.

SUMMARY OF THE INVENTION

As described above, a disposable diaper capable of effectively preventing the mixture of the urine and stool has not yet been disclosed so far, and thus has been longed for. In view of the conventional techniques as described above, it is an object of the present invention to provide a disposable diaper capable of definitely separating urine and stool discharged by a wearer and absorbing and retaining the separated urine and stool and which is capable of effectively preventing mixture of the urine and stool.

A disposable diaper according to a first aspect of the present invention includes an absorber, a top sheet disposed to cover an upper surface of the absorber and at least partially formed of a liquid permeable material, and a back sheet disposed to cover a lower surface of the absorber and formed of a liquid impermeable material. The disposable diaper further includes a skin contact sheet disposed above the top sheet, and formed with a stool passing opening, which is an opening capable of passing a stool therethrough, and a urine/stool separation wall disposed in a space between the skin contact sheet and the top sheet for separating the space into a front body part side and a back body part side. The urine/stool separation wall is formed of a breathable water repellent sheet.

According to a second aspect of the present invention, in the disposable diaper according to the first aspect of the present invention, while one end of the breathable water repellent sheet is joined to the skin contact sheet, the other end of the breathable water repellent sheet is dropped to a surface of the top sheet to form the urine/stool separation wall.

According to a third aspect of the present invention, in the disposable diaper according to the second aspect of the present invention, the other end of the breathable water repellent sheet is joined to the top sheet.

According to a fourth aspect of the present invention, in the disposable diaper according to either one of the first to third aspects of the present invention, a part of the surface of the top sheet is covered with the breathable water repellent sheet.

According to a fifth aspect of the present invention, in the disposable diaper according to either one of the first to fourth aspects of the present invention, to the skin contact sheet, a urine passing opening is formed and the urine/stool separation wall is disposed between the stool passing opening and the urine passing opening, and separates the space into a space communicating with the stool passing opening and a space communicating with the urine passing opening.

The disposable diaper according to the present invention can definitely separate the urine and stool discharged by the wearer and absorb and retain the separated urine and stool and can effectively prevent the mixture of the urine and stool.

DETAILED DESCRIPTION OF THE INVENTION

Specific description will now be made of preferred embodiments of the disposable diaper according to the present invention, taking a two-piece-type and pants-type diaper as an example. The present invention, however, widely includes disposable diapers which have particular features of the invention, and thus is not limited to the following embodiments. For drawing convenience, opening stretchable members, belly-surrounding stretchable members, and waist-surrounding stretchable members are eliminated from FIGS. 4 and 9, and joined parts where a breathable water repellent sheets which forms urine/stool separation walls and skin contact sheets or top sheets are joined are eliminated from FIGS. 7 to 9.

Figure 1:
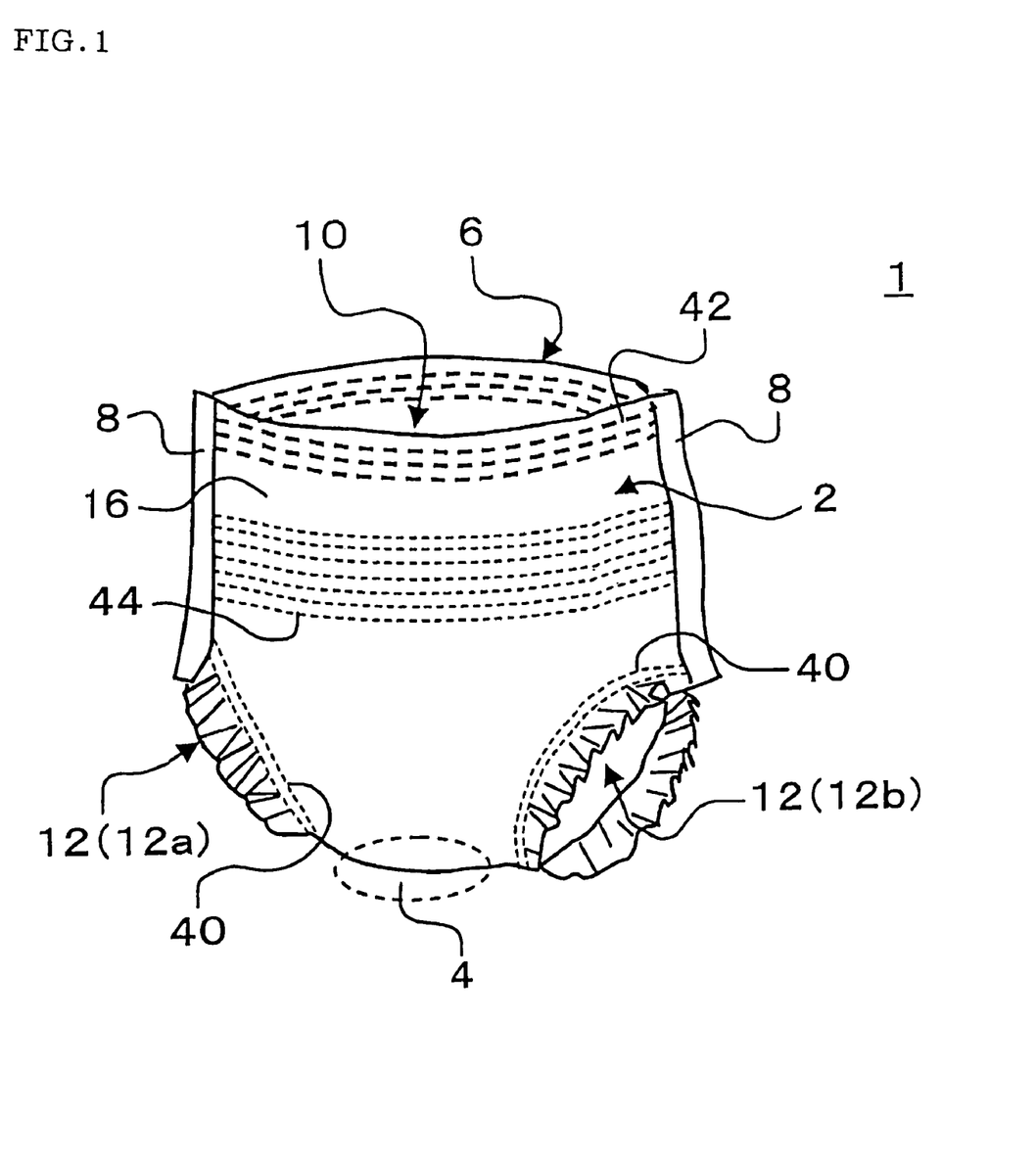
FIG. 1 is a schematic perspective view illustrating one embodiment of a disposable diaper according to the present invention, as viewed from the front side of the diaper.
Figure 2:
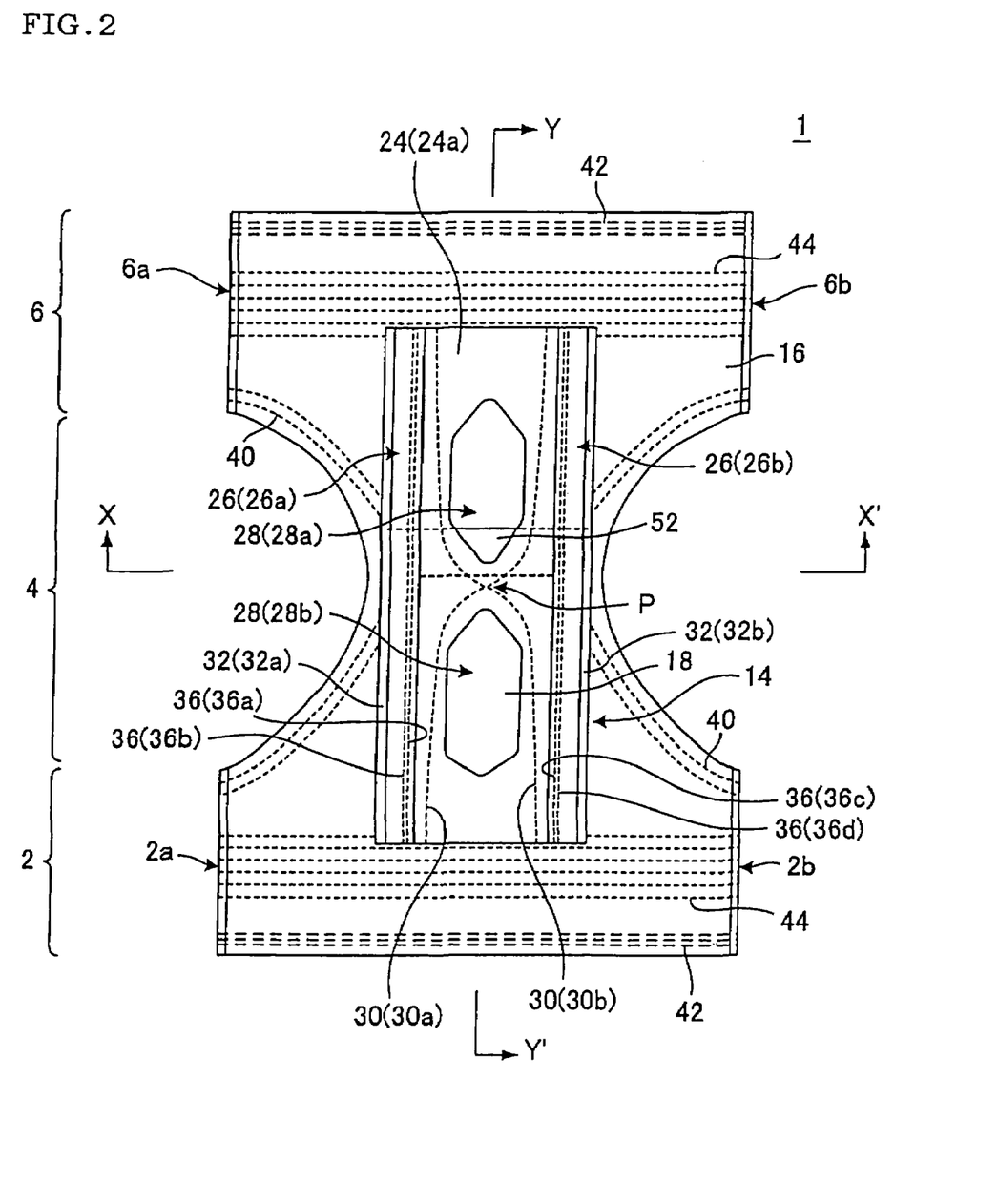
FIG. 2 is a plan view illustrating the one embodiment of the disposable diaper according to the present invention, as viewed from the side of an absorbent member of the disposable diaper when the diaper shown in FIG. 1 is unfolded.
Figure 3:
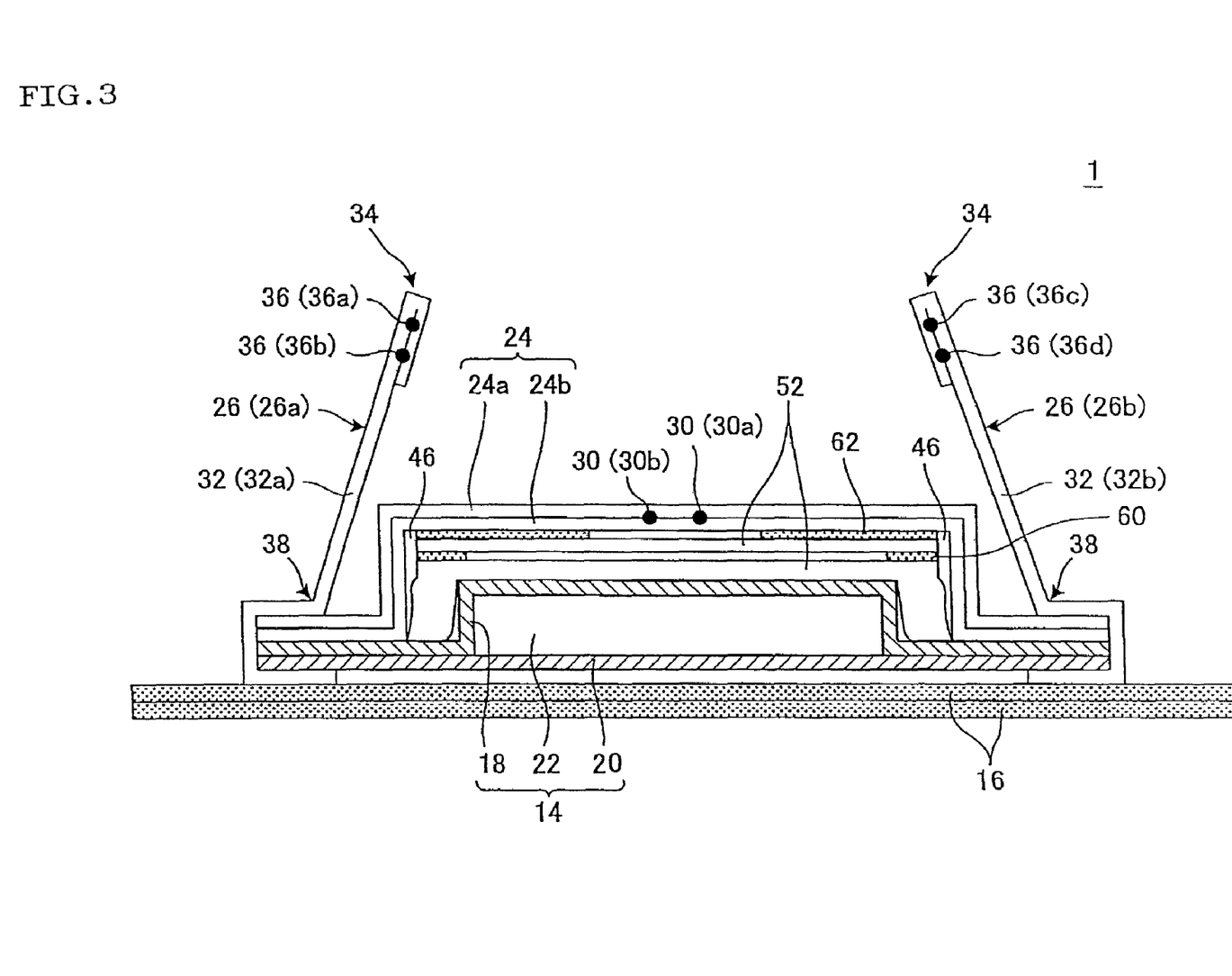
FIG. 3 is a schematic cross-sectional view illustrating the one embodiment of the disposable diaper according to the present invention, as cut along the X-X' line in the disposable diaper shown in FIG. 2.
Figure 4:
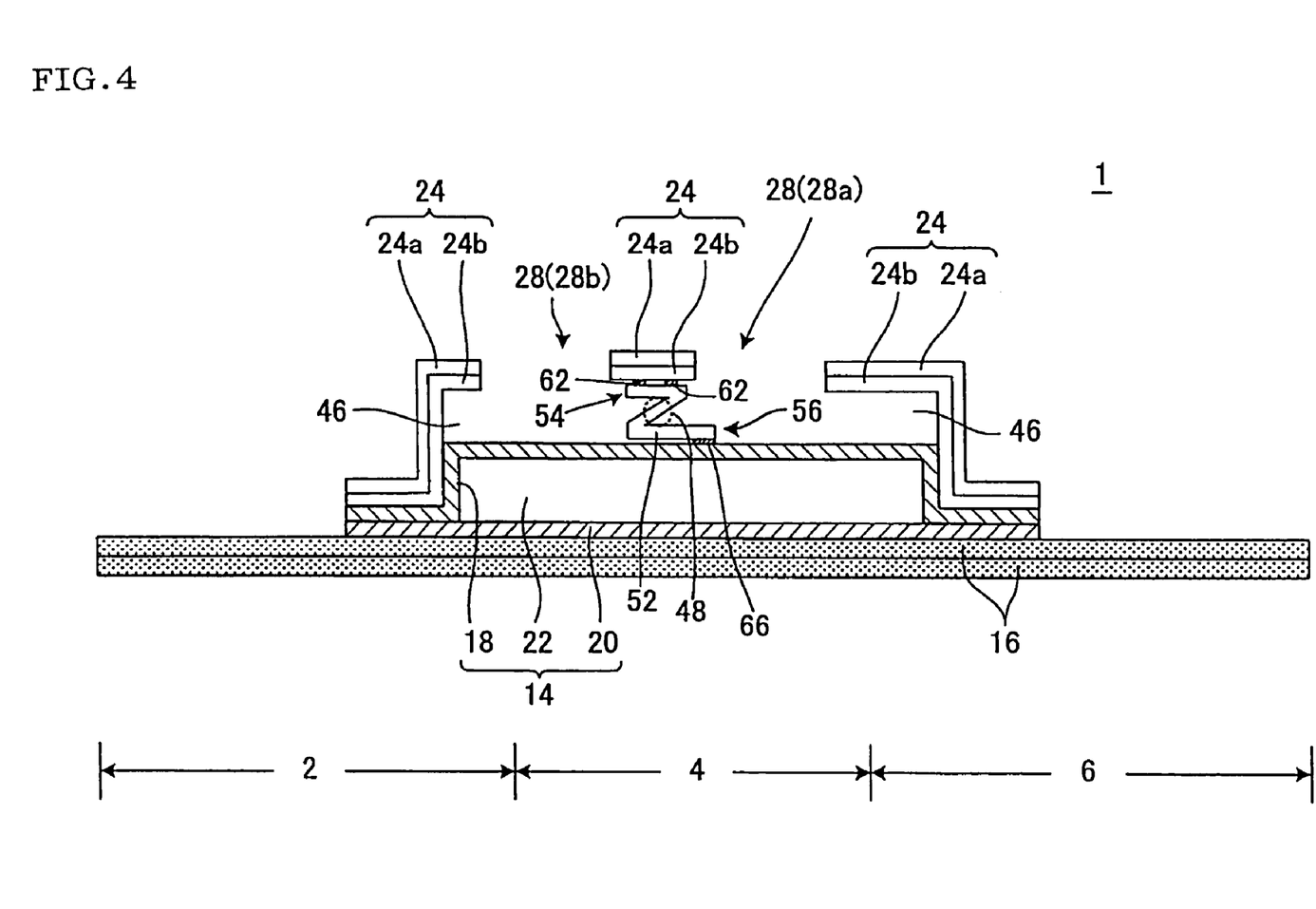
FIG. 4 is a schematic cross-sectional view illustrating the one embodiment of the disposable diaper according to the present invention, as cut along the Y-Y' line in the disposable diaper shown in FIG. 2.
Figure 5:
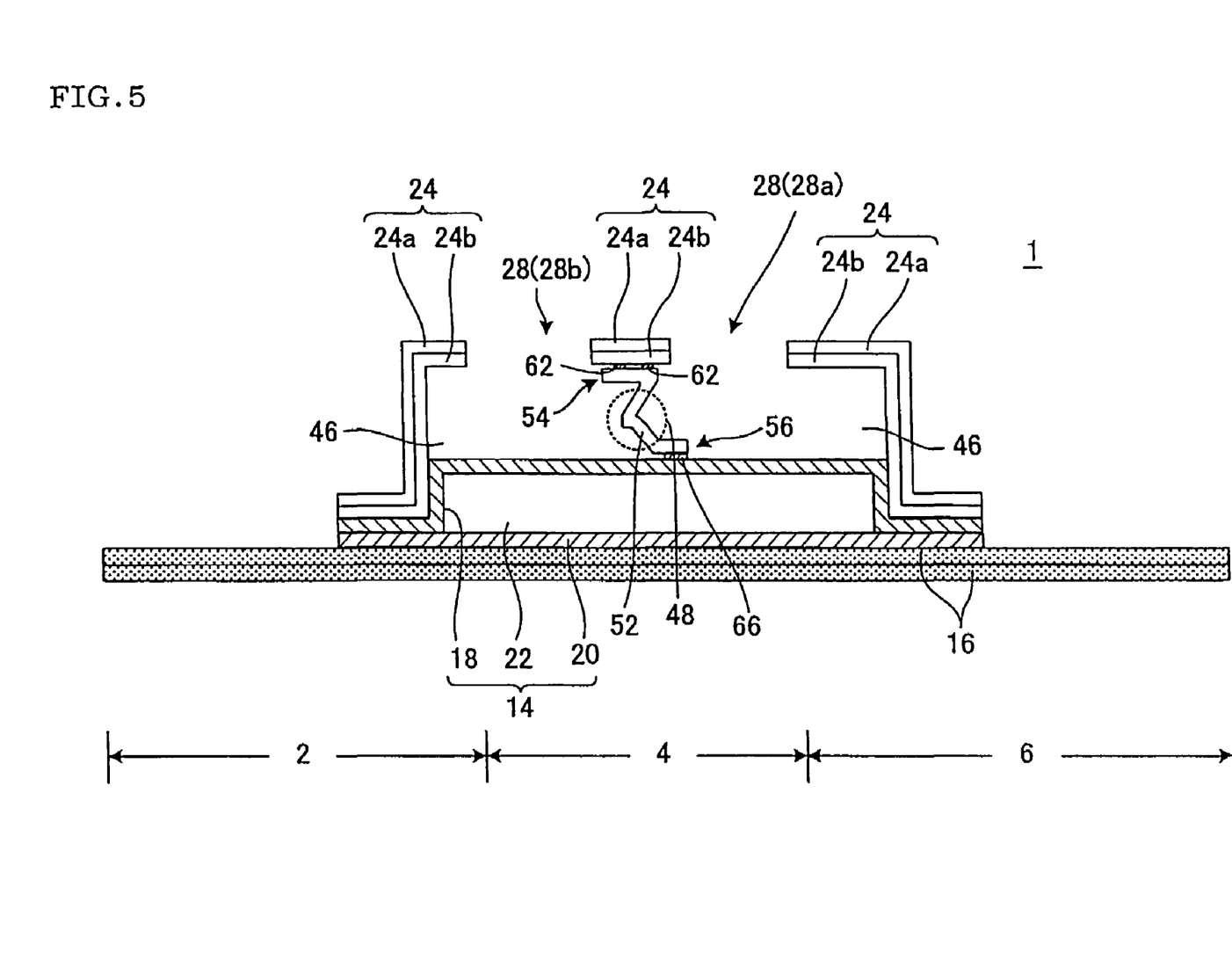
FIG. 5 is a schematic cross-sectional view illustrating a condition being used of the disposable diaper according to the present invention, as cut along the Y-Y' line in the disposable diaper shown in FIG. 2.

In the present specification, the "pants-type diaper" refers to a diaper preformed into a pants shape, as in the case of a disposable diaper 1 illustrated in FIGS. 1 and 2, in which corresponding side edges of a front body part 2 and a back body part 6 (i.e., side edges 2a and 6a and side edges 2b and 6b) are joined together to form joining parts 8, a waist-surrounding opening 10, and a pair of leg-surrounding openings 12a and 12b. Further, the "two-piece-type diaper" refers to a type of diaper in which an absorbent member 14 having a function of absorbing and retaining the excrement of a wearer of the diaper (i.e., an absorbing and retaining function) is separated from an exterior covering member 16 having a function of covering the body of the wearer (i.e., a fitting function) as a different member. As illustrated in FIGS. 3 to 5, the absorbent member 14 is a member including, as component parts thereof, an absorber 22, a top sheet 18, and a back sheet 20.

Further, in the present specification, the "front body part," refers to a part covering the ventral part (i.e., the front side of the body) of a wearer when the diaper is applied to the wearer, the "crotch part," refers to a part covering the crotch of a wearer when the diaper is applied to the wearer, and the "back body part" refers to a part covering the dorsal part (i.e., the back side of the body) of a wearer when the diaper is applied to the wearer, respectively.

[1] The structure of the disposable diaper according to the present invention: As in the case of the disposable diaper 1 illustrated in FIGS. 3 to 5 or the disposable diaper 100 illustrated in FIGS. 8 and 9, the disposable diaper according to the present invention is a disposable diaper including the absorber 22, the top sheet 18, and the back sheet 20. The disposable diaper further includes a skin contact sheet 24 which is disposed above the top sheet 18 and is formed with an opening capable of passing the stool therethrough (i.e., a stool passing opening 28a) and a urine/stool separation wall 48 disposed in a space 46 between the skin contact sheet 24 and the top sheet 18 to separate the space 46 into the front body part 2 side and the back body part 6 side.

[1-1] The skin contact sheet: The skin contact sheet is a member for separating the skin of the wearer from the top sheet, and is a sheet-shaped member disposed above the top sheet and formed with an opening capable of passing the stool therethrough (i.e., a stool passing opening). With the provision of the skin contact sheet, the skin of the wearer first contacts the skin contact sheet, and thus the top sheet disposed under the skin contact sheet does not easily come into direct contact with the skin of the wearer. That is, the skin of the wearer is separated from the top sheet. This also means that a shielding layer, i.e., the skin contact sheet intervenes between the top sheet and the skin of the wearer. Therefore, even if the stool remains on the top sheet, the effect of substantially decreasing the chance of direct contact of the stool with the skin of the wearer is obtained.

As the material forming the skin contact sheet, for example, a nonwoven fabric, a mesh sheet, a film, or the like made of such a resin as polyethylene, polypropylene, and polyester can be used. In particular, it is preferable to use the nonwoven fabric for the good texture against the skin. The above-described materials may be liquid permeable, liquid impermeable, or water repellent. It is preferable, however, that the above-described materials are water repellent materials (e.g., a water repellent nonwoven fabric) for the ability to maintain a dry texture (i.e., dryness) even after a long time wearing.

The skin contact sheet of the disposable diaper according to the present invention needs to be formed with the opening capable of passing therethrough the stool discharged by the wearer (i.e., the stool passing opening). With this structure, the stool discharged by the wearer drops on the top sheet through the skin contact sheet, and thus the chance of direct contact of the stool with the skin of the wearer can be substantially decreased.

There is no particular restriction on the shape of the stool passing opening, as long as the shape allows the passage of the stool. That is examples of the "opening" capable of passing the stool therethrough include a hole, such as a circular opening, an oval opening, and a rhombic opening, and also include a slit such as a straight-line slit, a cross-shape slit, and a star-shape slit formed by crossing three or more slits. Specifically, an oval opening, or a star-shape slit in which an anteroposterior direction (longitudinal direction) of the diaper is a long axis direction is preferred. The oval opening has an advantage that the stool can easily pass through the opening of the skin contact sheet, and the star-shape slit has an advantage of effectively preventing that the stool, once passed through the opening of the skin contact sheet and dropped onto the top sheet, from again being exposed from the opening of the skin contact sheet and contaminating the buttocks of the wearer.

Figure 7:
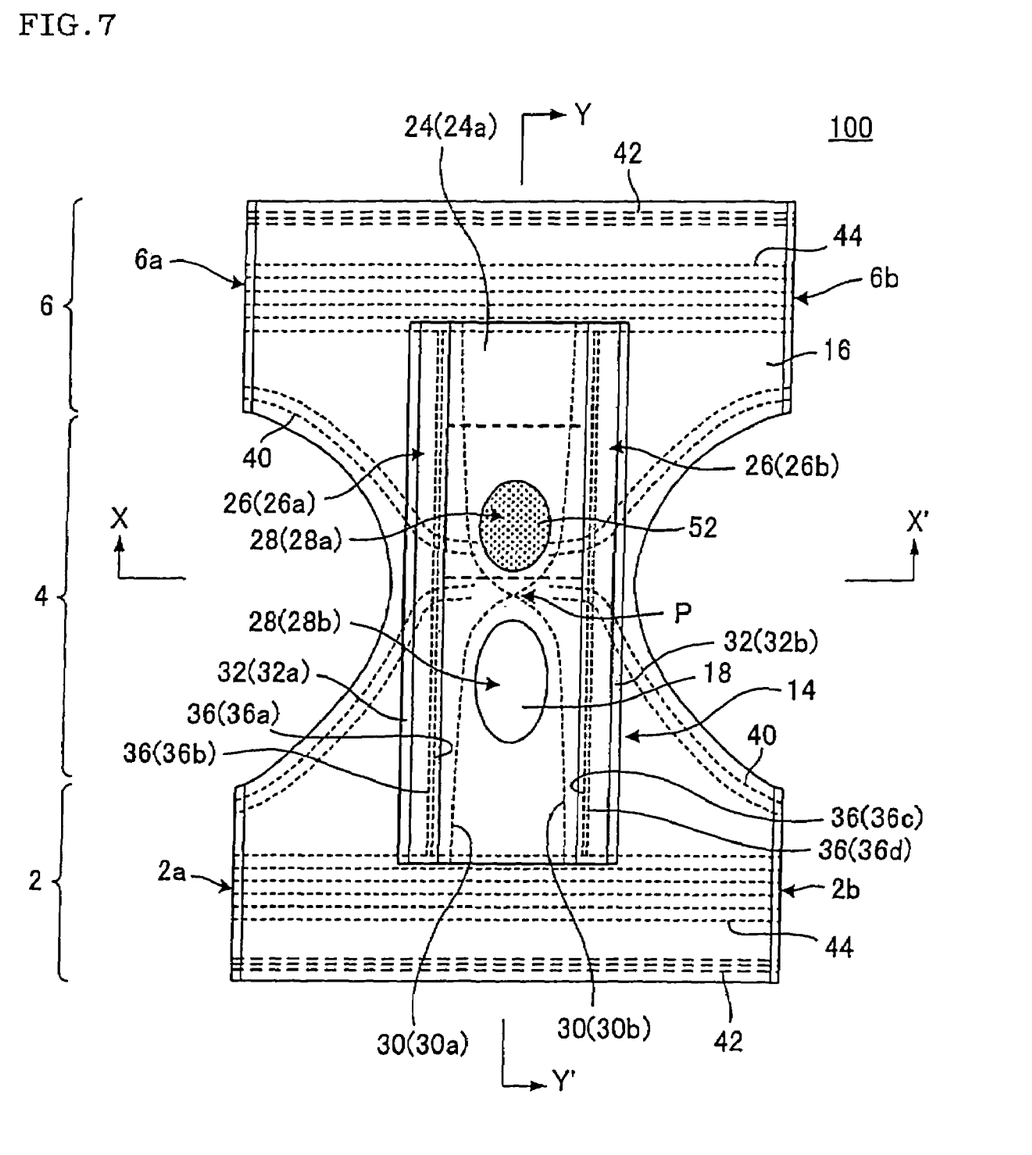
FIG. 7 is a plan view illustrating another embodiment of the disposable diaper according to the present invention, as viewed from the side of the absorbent member of the disposable diaper when the diaper is unfolded.

For example, the disposable diaper 1 illustrated in FIG. 2 is an example of a disposable diaper on which a substantially hexagonal opening long in an anteroposterior direction of the diaper and whose six angles has a round shape is formed to the part corresponding to a crotch part 4 of the skin contact sheet 24 as the stool passing opening 28a. The disposable diaper 100 illustrated in FIG. 7 is an example of a disposable diaper on which an oval opening whose anteroposterior direction is the long axis direction is formed to the part corresponding to the crotch part 4 of the skin contact sheet 24 as the stool passing opening 28a. Sizes of the hole and slit can be appropriately decided in consideration of the function of "passing the stool".

The skin contact sheet may be formed with a urine passing opening to a region toward the front body side from the stool passing opening. That is, it is preferable that the skin contact sheet is formed with the stool passing opening and the urine passing opening, as the openings.

With the formation of the urine passing opening as described above, it is possible to cause the urine discharged by the wearer to securely flow into the inside of the skin contact sheet through the opening. Thereby, it is possible to effectively prevent the urine from diffusing down the skin contact sheet and leaking sideward from the leg-surrounding openings and the like of the diaper. For instance, the disposable diaper 1 illustrated in FIG. 2 is an example in which, in addition to the stool passing opening 28a of the substantially hexagonal shape, a urine passing opening 28b of a substantially hexagonal shape whose six angles are formed in a round shape and angles of the front side of the diaper are formed as blunt angles is further formed on the skin contact sheet 24 as the opening 28. The disposable diaper 100 illustrated in FIG. 7 is an example in which, in addition to the stool passing opening 28a of the oval shape, a urine passing opening 28b of an oval shape is further formed on the skin contact sheet 24 as the opening 28. In this example, the stool passing opening 28a is formed at a portion corresponding to the crotch part 4 of the disposable diaper, and the urine passing opening 28b is formed at a portion toward the front body part 2 from the stool passing opening 28a.

It is preferable that a stretchable member (i.e., an opening stretchable member) is placed around the outer periphery of the opening. With the provision of the opening stretchable member, the skin contact sheet is applied with tension and thus becomes elastic. This contributes to an advantage that the skin contact sheet can be prevented from being crushed and sinking toward the top sheet, and that the skin contact sheet can easily come into contact with the skin of the wearer. Further, with the provision of the opening stretchable member, it is possible to generate force for causing the skin contact sheet to contract and causing the top sheet, the absorber, and the back sheet to bend toward the downside (i.e., toward the exterior covering member). Therefore, the skin contact sheet can be kept spaced from the top sheet, and the skin contact sheet and the top sheet can be definitely separated from each other. Further, with the contraction of the skin contact sheet, even if a space exists between the skin contact sheet or the top sheet and a breathable water repellent sheet to be a urine/stool separation wall, the space can be reduced. Accordingly, the space between the skin contact sheet and the top sheet can be definitely separated.

As the material for the opening stretchable member, stretchable materials used in conventional disposable diapers can be preferably used. Specifically, the material may be a rubber thread or a flat rubber string made of a natural rubber or a synthetic rubber (e.g., urethane rubber), a stretchable net, a stretchable film, stretchable foam (e.g., urethane foam), or the like.

There is no particular restriction on the arrangement pattern of the opening stretchable member, as long as the pattern allows the exertion of the above-described effects. To definitely apply the stretching force to the opening, however, it is preferable that the opening stretchable member is arranged in such a pattern to surround the peripheral rim of the opening. For example, it is preferable to arrange the opening stretchable member in such a pattern as a circular pattern, an oval pattern, or a rhombic pattern to surround the peripheral rim of the opening.

In another preferable embodiment, two opening stretchable members are used as the opening stretchable members and arranged in such a pattern to cross at least one point anterior or posterior to the opening so as to surround a part of the peripheral rim of the opening. With the opening stretchable members arranged in such a pattern, the opening stretchable members can be continuously arranged in the anteroposterior direction of the diaper. This is preferable in view of the advantage that the continuous manufacture of disposable diapers can be easily performed.

For example, the disposable diaper 1 illustrated in FIG. 2 and the disposable diaper 100 illustrated in FIG. 7 are examples in which two opening stretchable members 30a and 30b are used as the opening stretchable members 30 and arranged in such a pattern to cross at a point P between the stool passing opening 28a and the urine passing opening 28b so as to surround a part of the peripheral rim of each of the stool passing opening 28a and the urine passing opening 28b. With the opening stretchable members 30a and 30b arranged in such a pattern, it is possible to easily manufacture an absorbent member continuum in which the absorbent member 14 is continuously arranged in the longitudinal direction.

Further, in the disposable diaper 1 illustrated in FIG. 2, and the disposable diaper 100 illustrated in FIG. 7, the opening stretchable members 30a and 30b are arranged to cross at the center of the crotch part 4. With this arrangement, the stretching force in the width direction (i.e., the sideward direction of the diaper) can be applied more at the crotch part 4 (i.e., the proximity of the point P) than at the front body part 2 or the back body part 6 of the diaper. Therefore, there is an effect of making the skin of the wearer come into closer contact with a portion of the skin contact sheet 24 between the stool passing opening 28a and the urine passing opening 28b, which tends to sag with relative ease. Furthermore, in the disposable diaper 1 illustrated in FIG. 2, the opening stretchable members 30a and 30b do not cross at other points than the center point P of the crotch part 4. Thus, the opening stretchable members 30a and 30b are arranged in such a pattern that a part of the peripheral rim of the stool passing opening 28a at the side of the back body part 6 and a part of the peripheral rim of the urine passing opening 28b at the side of the front body part 2 are open. With this arrangement, portions of the skin contact sheet 24 at the sides of front body part 2 and the back body part 6 do not come into excessively close contact with the skin of the wearer, and thus the breathability can be ensured. Accordingly, perspiration due to the contact of the skin contact sheet is suppressed, and the stuffiness and the skin trouble attributable to the sweat can be effectively prevented.

The opening stretchable member as described above is fixed to the skin contact sheet with an adhesive agent or another medium. The method of fixing the opening stretchable member may be bonding with a hot-melt adhesive agent or another adhesive agent of high fluidity, or welding with heat or ultrasound such as heat-sealing, for example.

To apply sufficient stretching force to the opening, it is preferable to fix the opening stretchable member with the opening stretchable member stretched. For example, if the opening stretchable member is a natural rubber or a synthetic rubber, it is preferable to fix the opening stretchable member with the opening stretchable member stretched by 100 to 400%, and more preferably by 200 to 300%. With the opening stretchable member fixed with the stretching rate of the above range, it is possible to apply the sufficient stretching force to the opening and to prevent the opening from unnecessarily contracting.

There is no particular restriction on the method of arranging the opening stretchable member. However, as in the case of the disposable diaper 1 illustrated in FIG. 3 and the disposable diaper 100 illustrated in FIG. 7, for example, it is preferable to form the skin contact sheet 24 by pasting together two sheet members (i.e., an upper sheet 24a and a liner sheet 24b), and to place the opening stretchable members 30a and 30b to be sandwiched between the upper sheet 24a and the liner sheet 24b. The use of this arrangement method is preferable in that the stretching force can be applied to the skin contact sheet by the minimum necessary stretchable members.

Figure 8:
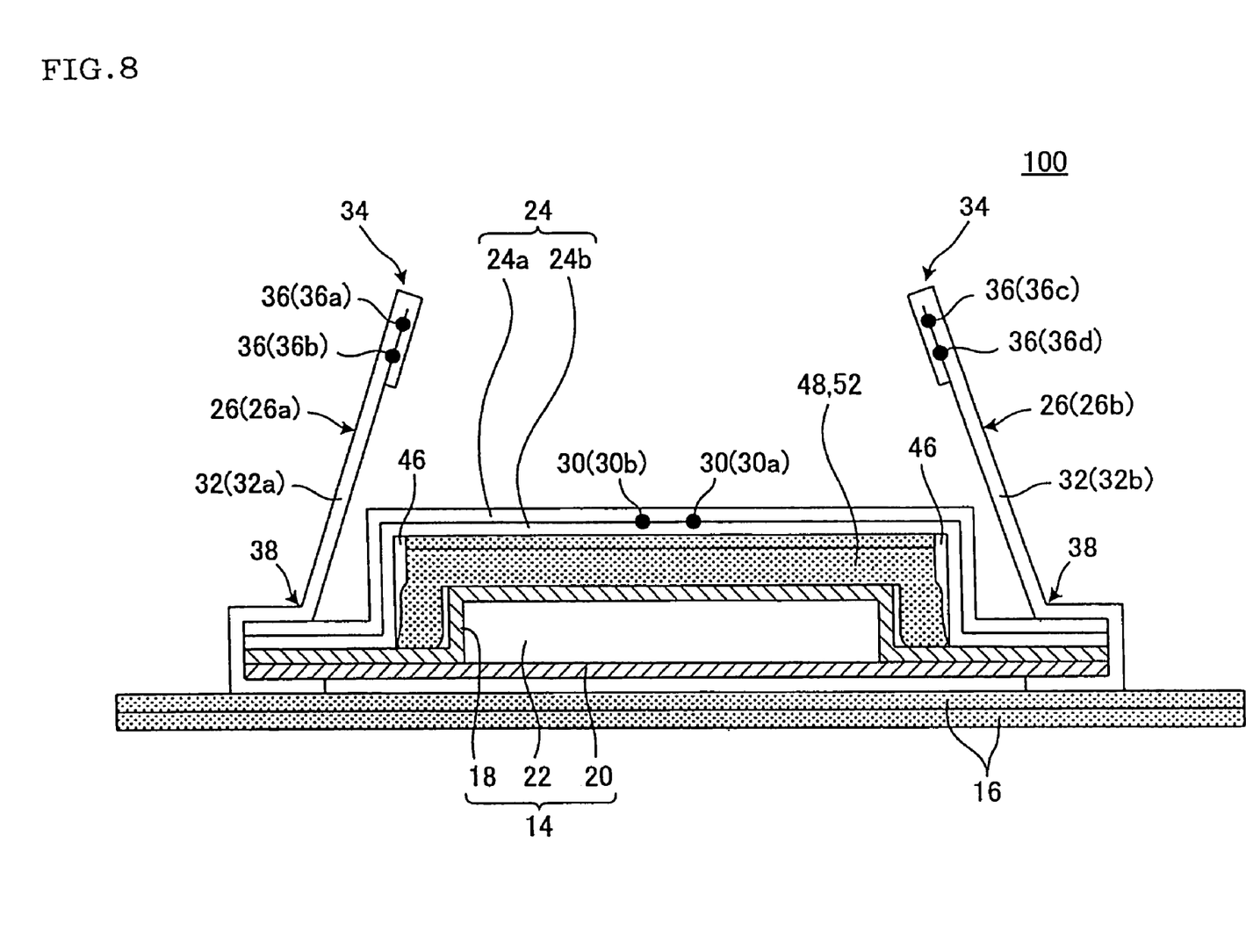
FIG. 8 is a schematic cross-sectional view illustrating still another embodiment of the disposable diaper according to the present invention, as cut along the X-X' line in the disposable diaper shown in FIG. 7.

The disposable diaper 1 illustrated in FIGS. 2 and 3 and the disposable diaper 100 illustrated in FIGS. 7 and 8 employ skin contact sheets which cover the entire of the surface of the top sheet 18 as the skin contact sheet 24. However, the skin contact sheet according to the present invention is not limited to such skin contact sheets but it is enough if a sheet member is disposed to an upper part than the surface of the top sheet.

The method of fixing the skin contact sheet includes, for example, (1) a method of fixing the skin contact sheet 24 such that the skin contact sheet 24 is inserted in portions where sheet members 32a and 32b, which form standing gathers 26a and 26b, respectively, are pasted with the top sheet 18 (or the back sheet 20), as in the case of the disposable diaper 1 illustrated in FIG. 3 and the disposable diaper 100 illustrated in FIG. 8, and (2) a method of fixing the skin contact sheet 24 to portions on the inside surfaces of the standing gathers between upper end edges and lower edges (i.e., standing lines) of the standing gathers. Alternatively, the skin contact sheet may be fixed in an inside region encompassed by the pair of the standing gathers without being in contact with the standing gathers. For example, there is (3) a method of fixing the skin contact sheet in portions where the top sheet and the back sheet of the absorbent member are pasted together (i.e., so-called flap portions) within the region encompassed by the standing gathers. The method (1) is preferable among the above methods in that the method is highly effective in making the skin contact sheet in close contact with the skin of the wearer.

[1-2] The urine/stool separation wall: The urine/stool separation wall is a member for separating urine and stool discharged by a wearer from each other. The urine/stool separation wall is made of a breathable water repellent sheet and disposed in a space between the skin contact sheet and the top sheet. With the provision of the urine/stool separation wall, the space between the skin contact sheet and the top sheet is separated into a front body part side and a back body part side at the boundary of the urine/stool separation wall, and the urine is introduced into the space of the front body part side and the stool is introduced into the space of the back body part side. Because the urine/stool separation wall is made of the breathable water repellent sheet, the urine which passed through the sheet and introduced into the front body part side does not permeate the back body part side. Accordingly, mixture of the urine and the stool can be effectively prevented and occurrence of diaper rash due to the mixture of the urine and the stool can be effectively prevented.

In the disposable diaper according to the present invention, it is necessary that the urine/stool separation wall is made of a breathable water repellent sheet. The breathable water repellent sheet is low in liquid permeability and is effective to prevent urine and loose stool from permeating the urine/stool separation wall and mixing each other. The urine/stool separation wall can be made of a liquid impermeable sheet such as the sheet used for the back sheet. However, if the liquid impermeable sheet such as plastic film is used, (1) because the liquid impermeable sheet does not have breathability, the inside of the sheet tends to be stuffy, and (2) because the liquid impermeable sheet has little flexibility and shape-fitting ability, fittedness to a body of a wearer is low. Further, in a case in which the liquid impermeable sheet exposes from the opening of the skin contact sheet and comes in contact with the body of the wearer, (3) the liquid impermeable sheet may have a harsh texture and tend to leave a wet feel on a surface. As in the case of disposable diaper according to the present invention, by forming the urine/stool separation wall with the breathable water repellent sheet, while the above-described disadvantages are prevented, an excellent effect to reduce the chance of mixing the urine and stool discharged by the wearer can be obtained.

As the material used for forming the breathable water repellent sheet, nonwoven fabrics such as a spunbond, or a card-emboss can be used. However, for the reason of high anti-hydraulic pressure, it is preferable to use nonwoven fabrics such as a SMS (spunbonded/meltblown/spunbonded) or a SMMS (spunbonded/meltblown/meltblown/spunbonded).

The breathable water repellent sheet can form the urine/stool separation wall by joining one end of the breathable water repellent sheet to the skin contact sheet and the other end is dropped to a surface of the top sheet. By joining one end of the breathable water repellent sheet to the skin contact sheet, it is possible to prevent the urine and stool passing through the space above the urine/stool separation wall and moving. With respect to the other end of the breathable water repellent sheet, it is preferable that the other end is joined to the top sheet. By joining the other end of the breathable water repellent sheet to the top sheet, the urine/stool separation wall is strongly fixed without displacement and the space between the skin contact sheet and the top sheet is definitely separated into the front body part side and the back body part side.

Figure 9:
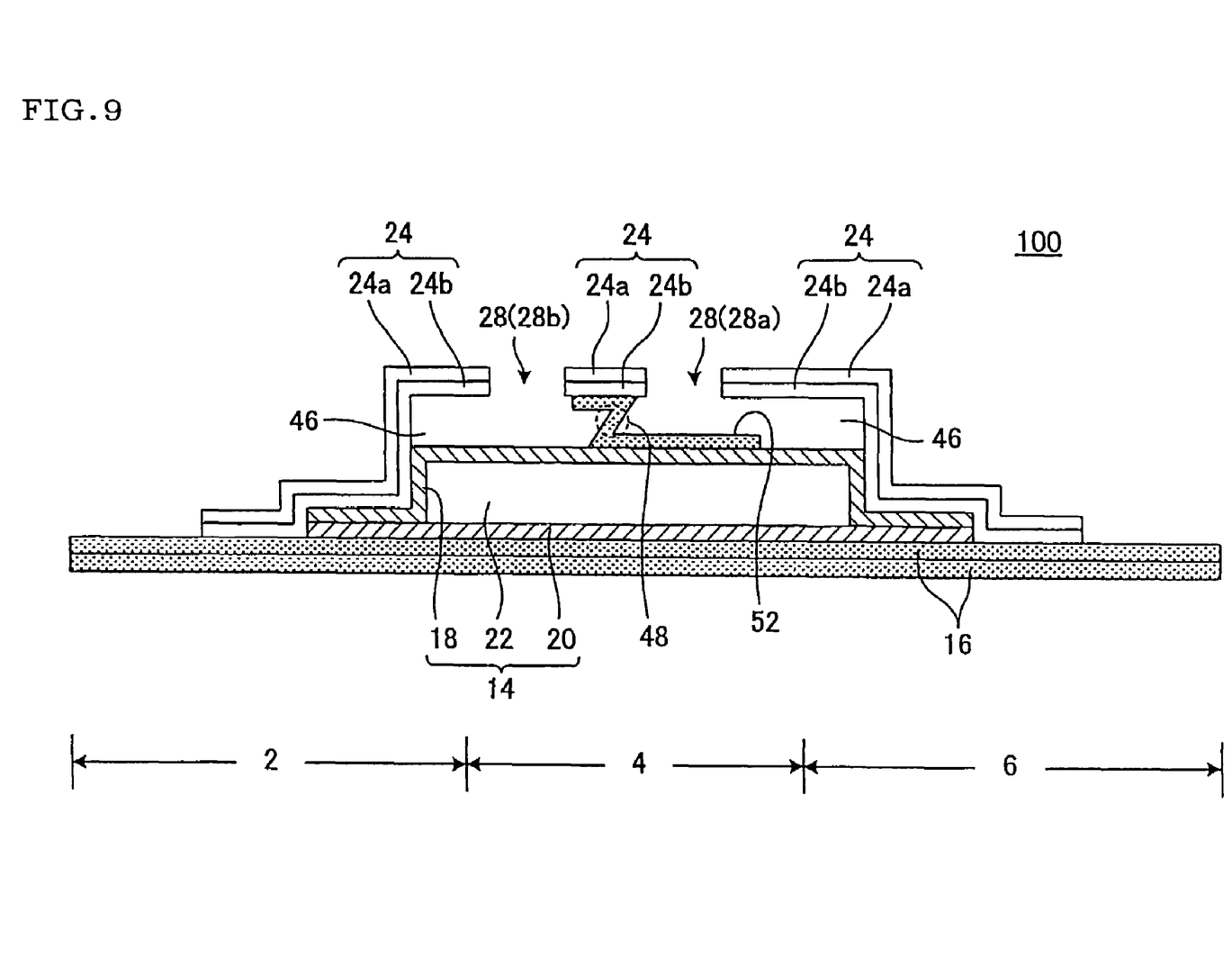
FIG. 9 is a schematic cross-sectional view illustrating one embodiment of the disposable diaper according to the present invention, as cut along the IX-IX line in the disposable diaper shown in FIG. 7.

For example, the disposable diaper 1 illustrated in FIGS. 3 and 4 and the disposable diaper 100 illustrated in FIGS. 8 and 9 are examples in which to a surface (i.e., lower surface) of the liner sheet 24b which forms the skin contact sheet 24, one end of a breathable water repellent sheet 52 which forms the urine/stool separation wall 48 is joined, and the other end is dropped to the surface of the top sheet 18, then, joined to the surface (i.e., upper surface) of the top sheet 18.

In the disposable diaper according to the present invention, by making the distance between the one end of the breathable water repellent sheet (i.e., the joined part of the skin contact sheet side) and the other end (i.e., the joined part of the top sheet side) long, it is possible to make the standing height of the urine/stool separation wall high, and definitely separate the skin contact sheet from the top sheet. In this case, it is preferable that the breathable water repellent sheet is folded once or a plurality of times between the one end and the other end. With such a structure, as shown in FIG. 5, it is possible to form a folded part which is extensible in upward and downward directions in the urine/stool separation wall 48. The folded part extends as the skin contact sheet 24 separates from the top sheet 18 at a time of use of the diaper, and the standing height of the urine/stool separation wall 48 can be ensured. If the folded part has been formed, it is preferable in that the urine/stool separation wall 48 is hard to restrict the movement of the skin contact sheet 24. Further, in a case in which the breathable water repellent sheet is formed to be long, there is a feature that the surface of the top sheet right under the stool passing opening or the urine passing opening is not easily covered by the breathable water repellent sheet. Accordingly, there is an advantage that a disadvantage which is described below that absorption of urine is inhibited by the breathable water repellent sheet is hard to be occurred.

The method of folding the breathable water repellent sheet can include methods to fold the breathable water repellent sheet so that a cross section viewed from the side surface side becomes to be a Z-shape (folded twice), a M-shape (folded three times), or an accordion shape (folded many times). For example, the disposable diaper 1 illustrated in FIG. 4 and the disposable diaper 100 illustrated in FIG. 7 are examples in which the breathable water repellent sheet 52 is folded to have a Z-shaped cross section (the folding method may be referred to as a "Z folding") and one end of the breathable water repellent sheet 52 is joined to the skin contact sheet 24 and the other end is joined to the top sheet 18. In these examples, the other parts (for example, the folded parts) except for an end 54 and the other end 56 of the breathable water repellent sheet 52 are formed to be non-joined state to the skin contact sheet 24 and the top sheet 18.

In the disposable diaper according to the present invention, it is enough if the space between the skin contact sheet and the top sheet is separated into the front body part side and the back body part side, and it is not necessary that the space is completely sectionalized. For example, in the disposable diaper 1 illustrated in FIG. 3, although spaces exist at both sides of the urine/stool separation wall 48 and spaces 46 communicate between the front body part side and the back body part side. The disposable diaper of such type is also effective to reduce the chance that the urine and the stool discharged by the wearer mix with each other, and included in the scope of the present invention. That is, because the absorber 22 is deformed to have a U-shaped cross section at a time of use of the disposable diaper, practically, the urine or the stool does not pass through the space, and, generally, the discharged urine is quickly absorbed into the absorber, the possibility that unabsorbed urine passes through the space and flows into a space of the back body part side is little.

In the disposable diaper according to the present invention, by making the joined position of the breathable water repellent sheet to the skin contact sheet come into close contact with the joined position of the breathable water repellent sheet to the top sheet, that is, by making the distance between the both joined positions in the anteroposterior direction of the disposable diaper be short, the area of the top sheet surface right under the stool passing opening or the urine passing opening to be covered by the breathable water repellent sheet can be reduced. For example, if the wearer is a girl, an application position (an anteroposterior position) of the disposable diaper is easily displaced, and urine may flow into the space between the skin contact sheet and the top sheet from the stool passing opening. In such a case, if the area of the top sheet surface right under the stool passing opening to be covered by the breathable water repellent sheet dropped onto the surface of the top sheet is large, the absorption of the urine into the absorber at the part is inhibited, and this may cause urine leakage. Accordingly, it is preferable by making the joined position of the breathable water repellent sheet to the skin contact sheet come into close contact with the joined position of the breathable water repellent sheet to the top sheet, (that is, by making the distance between the both joined positions in the anteroposterior direction of the disposable diaper be short), to reduce the area of the top sheet surface right under the stool passing opening or the urine passing opening to be covered by the breathable water repellent sheet.

As described above, in the case of making the joined position of the breathable water repellent sheet to the skin contact sheet come into close contact with the joined position of the breathable water repellent sheet to the top sheet, (that is, making the distance between the both joined positions in the anteroposterior direction of the disposable diaper be short), it is preferable that the area of the top sheet surface right under the stool passing opening or the urine passing opening to be covered by the breathable water repellent sheet joined to the top sheet is, in both cases of a disposable diaper for adult and a disposable diaper for infant, 50 area % or less than 50 area % of the area of the opening, and more preferably, 30 area % or less than 30 area % of the area of the opening. For example, the disposable diaper 1 illustrated in FIGS. 2 and 4 are examples of disposable diapers for infant, in which a distance between joined parts 62b and 62d and a joined part 66 is formed to be short, and the surface of the top sheet 18 right under the stool passing opening 28a is covered by the breathable water repellent sheet 52 by an amount corresponding to about 30% of the opening area of the stool passing opening.

In the disposable diaper according to the present invention, by the folded part of the breathable water repellent sheet, the surface of the top sheet right under the stool passing opening or the urine passing opening can be covered. Because the folded part of the breathable water repellent sheet is not joined to the top sheet and can freely move, the above-described disadvantage that the absorption of the urine into the absorber is inhibited and causes the urine leakage is hard to occur.

On the other hand, in the disposable diaper according to the present invention, it is also preferable that a part of the surface of the top sheet is covered with the breathable water repellent sheet. With such a structure, there is an advantage that even if urine which passed through the top sheet from the space of the front body part side is not absorbed by the absorber, moves to the back body part side, and oozes through the surface of the top sheet, it can be prevented that the urine and the stool come into direct contact with each other.

For example, the disposable diaper 100 illustrated in FIGS. 7 and 9 is an example in which one end of the breathable water repellent sheet 52 is joined to the skin contact sheet 24, and the breathable water repellent sheet 52 is dropped to the surface of the top sheet 18, and further disposed to cover a part of the surface of the back body part 6 side of the top sheet 18. In this example, in the surface of the top sheet 18, a part including right under the stool passing opening 28a is covered by the breathable water repellent sheet 52.

In the disposable diaper according to the present invention, it is preferable that the urine/stool separation wall is disposed to the crotch part and more preferably, disposed to a part which can be applied to a perineum of a wearer. With the provision of the urine/stool separation wall to such a part, the urine and stool discharged by the wearer can be definitely separated with each other. For example, the disposable diaper 1 illustrated in FIG. 4 is and example in which the urine/stool separation wall 48 is disposed to the crotch part 4, and more specifically, to the part which can be applied to the perineum of the wearer.

If two openings, that is, the stool passing opening and the urine passing opening are formed on the skin contact sheet, it is preferable that the urine/stool separation wall is disposed between the stool passing opening and the urine passing opening. With the provision of the urine/stool separation wall to such a position, the space between the skin contact sheet and the top sheet can be separated into a space communicating with the stool passing opening and a space communication with the urine passing opening. Accordingly, the urine and stool discharged by the wearer can be definitely separated with each other. For example, the disposable diaper 1 illustrated in FIG. 4 is an example in which the urine/stool separation wall 48 is disposed between the stool passing opening 28a and the urine passing opening 28b to separate into the front body part 2 side and the back body part 6 side of the disposable diaper.

There is no particular restriction on the length of the breathable water repellent sheet which forms the urine/stool separation wall, a desired length of the breathable water repellent sheet can be used in consideration of a height of the urine/stool separation wall (i.e., the space between the skin contact sheet and the top sheet), a size of the folded part, a joined position, and the like.

[1-3] The absorber: The absorber is a member for absorbing and retaining the urine of the wearer. The absorber is made of an absorbent material due to the need to absorb and retain the urine and the body fluid of the wearer.

The absorbent material forming the absorber includes conventionally known absorbent materials usually used in the disposable diaper and other absorbent products, such as fluff pulp, super absorbent polymer (hereinafter refereed to as SAP), and a hydrophilic sheet, for example. It is preferable to use wood pulp or non-wood pulp fibrillated into floc as the fluff pulp, to use sodium polyacrylate as the SAP, and to use tissue, an absorbent paper, or a hydrophilicized nonwoven fabric as the hydrophilic sheet.

Each of these absorbent materials is usually used in the form of a single-layer mat or a multiple-layer mat. In such a case, a single type of the above absorbent materials may be independently used, or two or more types of the absorbent materials may be used in combination. In particular, it is preferable to use approximately 10 to 500 parts by mass of the SAP with respect to 100 parts by mass of the fluff pulp. In this case, the SAP may be evenly mixed in each of the fluff pulp mats or may be placed in layers between a plurality of fluff pulp layers.

It is preferable that the absorber is interposed between at least parts of the top sheet and the back sheet. Usually, the absorber is sandwiched between the top sheet and the back sheet, and the peripheral rim of the absorber is sealed by adhesion so that the absorber is interposed between the top sheet and the back sheet. Therefore, the flap portions, in which the absorber is not interposed between the top sheet and the back sheet, are formed around the peripheral rim of the absorber.

It is preferable the entire absorber is wrapped by a hydrophilic sheet. This structure provides an advantage in that the SAP is prevented from leaking from the absorber and that the absorber is provided with the shape stability.

There is no particular restriction on the shape of the absorber. The shape of the absorber includes the shapes used in the conventional disposable diaper and other absorbent products, such as a rectangular shape, an hourglass shape, a calabash shape, and a T-shape, for example.

[1-4] The top sheet: The top sheet is a sheet disposed to cover the upper surface of the absorber (i.e., the surface at the side of the skin of the wearer when the diaper is applied to the wearer). The top sheet is at least partially (i.e., a part or the entirety of the top sheet is) made of a liquid permeable material due to the need to cause the absorber disposed at the side of the lower surface of the top sheet to absorb the urine of the wearer.

The liquid permeable material forming the top sheet includes a woven fabric, a nonwoven fabric, and a porous film, for example. In particular, it is preferable to use a hydrophilicized nonwoven fabric made of a thermoplastic resin such as polypropylene, polyethylene, polyester, or nylon.

The top sheet may be formed by a single sheet material. Alternatively, the top sheet may be formed by a plurality of sheet materials. For example, in an embodiment of a tape-type diaper later described, a top sheet (i.e., a center sheet) made of a liquid permeable material is disposed at the center of the diaper, and another top sheet (i.e., a side sheet) made of a water repellent material is disposed at side flap portions of the diaper.

[1-5] The back sheet: The back sheet is a sheet disposed to cover the lower surface of the absorber (i.e., the surface at the side of the clothes of the wearer when the diaper is applied to the wearer). The back sheet is made of a liquid impermeable material due to the need to prevent the urine of the wearer from leaking to the outside of the diaper.

The liquid impermeable material forming the back sheet includes, for example, a liquid impermeable film made of a resin such as polyethylene. In particular, it is preferable to use a microporous polyethylene film. The microporous polyethylene film is formed with a multitude of micro holes of a size of 0.1 to a few micrometers. The microporous polyethylene film is liquid impermeable but moisture permeable, and thus has an advantage of capable of preventing the inside of the diaper from becoming stuffy.

A sheet member (i.e., a cover sheet) may be pasted to the outer surface of the back sheet. The cover sheet is used to reinforce the back sheet and to improve the hand feeling (i.e., the tactile feeling) of the back sheet.

The material forming the cover sheet includes a woven fabric and a nonwoven fabric, for example. In particular, it is preferable to use a dry or wet nonwoven fabric made of a thermoplastic resin such as polyethylene, polypropylene, or polyester.

[1-6] The absorbent member: In the two-piece-type and pants-type diaper, the top sheet, the back sheet, and the absorber are formed as one member, i.e., the "absorbent member" having the absorbing and retaining function, and the absorbent member is joined with the exterior covering member, which has been manufactured separately from the absorbent member. Thereby, the disposable diaper is formed. In the absorbent member, as in the case of a sanitary napkin or the like, the top sheet and the back sheet are disposed on the upper surface and the lower surface of the absorber, respectively, so that the absorber is interposed between the top sheet and the back sheet. For example, the disposable diaper 1 illustrated in FIGS. 3 and 4 and the disposable diaper 100 illustrated in FIGS. 8 and 9 are examples in which the absorbent member 14 is formed by inserting the absorber 22 between the top sheet 18 and the back sheet 20 and adhering and sealing the peripheral rim of the absorber 22 to make the absorber 22 interposed between the top sheet 18 and the back sheet 20.

The absorbent member is formed into such a size to cover at least the crotch part of the diaper. To ensure the leakage preventing effect, however, it is preferable to form the absorbent member into such a size to cover not only the crotch part but also a part of the front body part and the back body part. The absorbent member can be fixed to the exterior covering member with the hot-melt adhesive agent or the like, for example.

[1-7] The exterior covering member: The exterior covering member is a member having the fitting function of covering the body of the wearer. Specifically, the exterior covering member is a sheet-shaped member for forming respective parts of the front body part, the crotch part, and the back body part.

In the two-piece-type and pants-type diaper, the absorbing and retaining function of absorbing and retaining the excrement of the wearer is performed solely by the absorbent member, and thus there is no need to use the liquid impermeable material as the material forming the exterior covering member. The material forming the exterior covering member includes, for example, a nonwoven fabric formed by a synthetic fiber of polyethylene, polypropylene, polyester, or another thermoplastic resin.

The exterior covering member is fixed, with such members as the leg-surrounding stretchable members inserted in the exterior covering member. In many cases, therefore, the exterior covering member is formed by pasting together two or more nonwoven fabrics. For example, the disposable diaper 1 illustrated in FIG. 2 and the disposable diaper 100 illustrated in FIG. 7 are examples in which the exterior covering member 16 is formed by two nonwoven fabrics, and leg-surrounding stretchable members 40, waist-surrounding stretchable members 42, and belly-surrounding stretchable members 44 are inserted and fixed between the two nonwoven fabrics.

[1-8] The respective stretchable members: In the pants-type disposable diaper, the leg-surrounding stretchable members and the waist-surrounding stretchable members are generally provided, and it is preferable to further provide the belly-surrounding stretchable members.

The leg-surrounding stretchable members are stretchable members placed along the respective leg-surrounding openings. With the provision of the leg-surrounding stretchable members, highly stretchable gathers (i.e., leg gathers) can be formed around the leg-surrounding openings. Accordingly, a clearance gap is not easily formed around the legs, and the leakage of the urine from the leg-surrounding openings can be effectively prevented.

The waist-surrounding stretchable members are stretchable members placed along the waist-surrounding opening. With the provision of the waist-surrounding stretchable members, a highly stretchable gather (i.e., a waist gather) can be formed around the waist-surrounding opening. With the waist gather, a clearance gap is not easily formed around the waist, and the leakage of the urine from the area around the waist can be prevented. Further, the fittedness of the diaper to the wearer is improved, and thus the diaper is prevented from slipping down.

The belly-surrounding stretchable members are stretchable members placed in a portion between the waist-surrounding opening and the leg-surrounding openings (i.e., a portion corresponding to the area around the belly of the wearer). With the provision of the belly-surrounding stretchable members, a highly stretchable tummy gather can be formed around the belly of the wearer. Coupled with the waist gather, the tummy gather can further improve the fittedness of the diaper and the effect of preventing the slide down of the diaper.

The disposable diaper 1 illustrated in FIGS. 1 and 2 and the disposable diaper 100 illustrated in FIG. 7 are examples in which a plurality of the leg-surrounding stretchable members 40 are placed around the peripheral rims of the leg-surrounding openings 12a and 12b, and a plurality of the waist-surrounding stretchable members 42 are placed around the peripheral rim of the waist-surrounding opening 10 so as to surround the waist-surrounding opening 10. Further, a plurality of the belly-surrounding stretchable members 44 are placed in the portion between the waist-surrounding opening 10 and the leg-surrounding openings 12a and 12b (i.e., the portion corresponding to the area around the belly of the wearer) so as to surround the belly of the wearer.

Each of these stretchable members can employ a similar structure to the structure used in the opening stretchable member described above. Further, the material forming the stretchable member, the elongation rate of the material, the elongated state of the stretchable member when the stretchable member is fixed, and the like can be determined in consideration of such factors as the extent of contraction of the gather.

[1-9] The standing gathers: To prevent sideward leakage of the urine discharged by the wearer, standing gathers can be included. The standing gathers are members for preventing the sideward leakage of the urine discharged by the wearer, and are leakage preventing walls structured to stand three-dimensionally. With the provision of the standing gathers, even if the urine is discharged on the skin contact sheet and diffuses down the skin contact sheet, the standing gathers function as breakwaters, and the leakage from the leg-surrounding openings and the like of the diaper (i.e., the so-called sideward leakage) can be effectively prevented. Incidentally, the word "standing gather(s)" may be expressed as "barrier cuff".

The standing gather can employ a similar structure to the structure used in the conventional disposable diaper and other absorbent products. For example, by providing a stretchable member (i.e., a standing gather stretchable member) on a part of a sheet member, a gather (i.e., folds) formed on the sheet member by the standing gather stretchable member can be preferably used.

The disposable diaper 1 illustrated in FIGS. 2 and 3 and the disposable diaper 100 illustrated in FIGS. 7 and 8 are examples in which sheet members 32a and 32b which are different from the top sheet 18 and the back sheet 20 are pasted to both side end parts of the absorbent member 14, and structured to be able to stand three-dimensionally from a standing line 38 to form a pair of standing gathers 26a and 26b. In this example, an edge portion of each of the sheet members 32a and 32b (i.e., an edge portion corresponding to the upper end edge 34 of each of the standing gather 26a and 26b) is folded, and the folded portion tucks therein the two standing gather stretchable members 36a and 36b or the two standing gather stretchable members 36c and 36d.

[2] The manufacturing method: An embodiment of the method of manufacturing the disposable diaper according to the present invention will now be described, taking an example in which the disposable diaper 1 illustrated in FIGS. 1 to 6 (i.e., the two-piece-type and pants-type diaper) is manufactured.

[2-1] The manufacture of the absorbent member: The absorber 22 wrapped by a hydrophilic sheet is disposed on the upper surface of the back sheet 20, and the top sheet 18 is disposed on the upper surface of the absorber 22. Then, the peripheral rim of the absorber 22 is sealed by adhesion, sandwiched by the top sheet 18 and the back sheet 20. Thereby, the absorbent member 14 is obtained.

[2-2] The manufacture of the skin contact sheet: The upper sheet 24a is pasted on the upper surface of the liner sheet 24b, with the two opening stretchable members 30a and 30b arranged in a predetermined pattern. In this case, the two opening stretchable members 30a and 30b are arranged in such a pattern to cross at the point P between the stool passing opening 28a and the urine passing opening 28b, which are later formed, and to surround a part of the peripheral rim of each of the stool passing opening 28a and the urine passing opening 28b.

Subsequently, the stool passing opening 28a and the urine passing opening 28b are formed on the liner sheet 24b and the upper sheet 24a, which have been pasted together. Thereby, the double-layer structured skin contact sheet 24 is obtained in which the two opening stretchable members 30a and 30b are arranged in such a pattern to cross at the point P between the stool passing opening 28a and the urine passing opening 28b, and to surround a part of the peripheral rim of each of the stool passing opening 28a and the urine passing opening 28b.

Further, one end 54 of the breathable water repellent sheet 52 which is folded in a Z-shape (to be the urine/stool separation wall 48 later) is pasted onto a position where is the surface (i.e., lower surface) of the liner sheet 24b and is between the stool passing opening 28a and the urine passing opening 28b, and fixed (i.e., joined parts 62a, 62b, 62c, and 62d). Thereby, the skin contact sheet 24 provided with the breathable water repellent sheet 52 which is later to be the urine/stool separation wall 48 can be obtained. Then, the breathable water repellent sheet is not limited to the Z-folded sheet, but a breathable water repellent sheet which is folded several times may be used. The fixation may be performed by using conventionally known bonding methods used for manufacturing a disposable diaper such as bonding with an adhesive such as a hot-melt adhesive agent, heat-bonding such as heat-sealing, ultrasound-sealing, emboss roll, and the like, pressure-bonding, and the like. The disposable diaper 1 illustrated in FIG. 4 is an example in which the one end 54 of the breathable water repellent sheet 52 is pasted onto the surface (i.e., the lower surface) of the liner sheet 24b with a hot-melt adhesive agent, joined, and fixed.

[2-3] The manufacture of the standing gathers: One edge portion of the sheet member 32a or 32b is folded, and the two standing gather stretchable members 36a and 36b or 36c and 36d are tucked in and pasted to the obtained folded portion. Thereby, the standing gather 26a or 26b is obtained.

Figure 6:
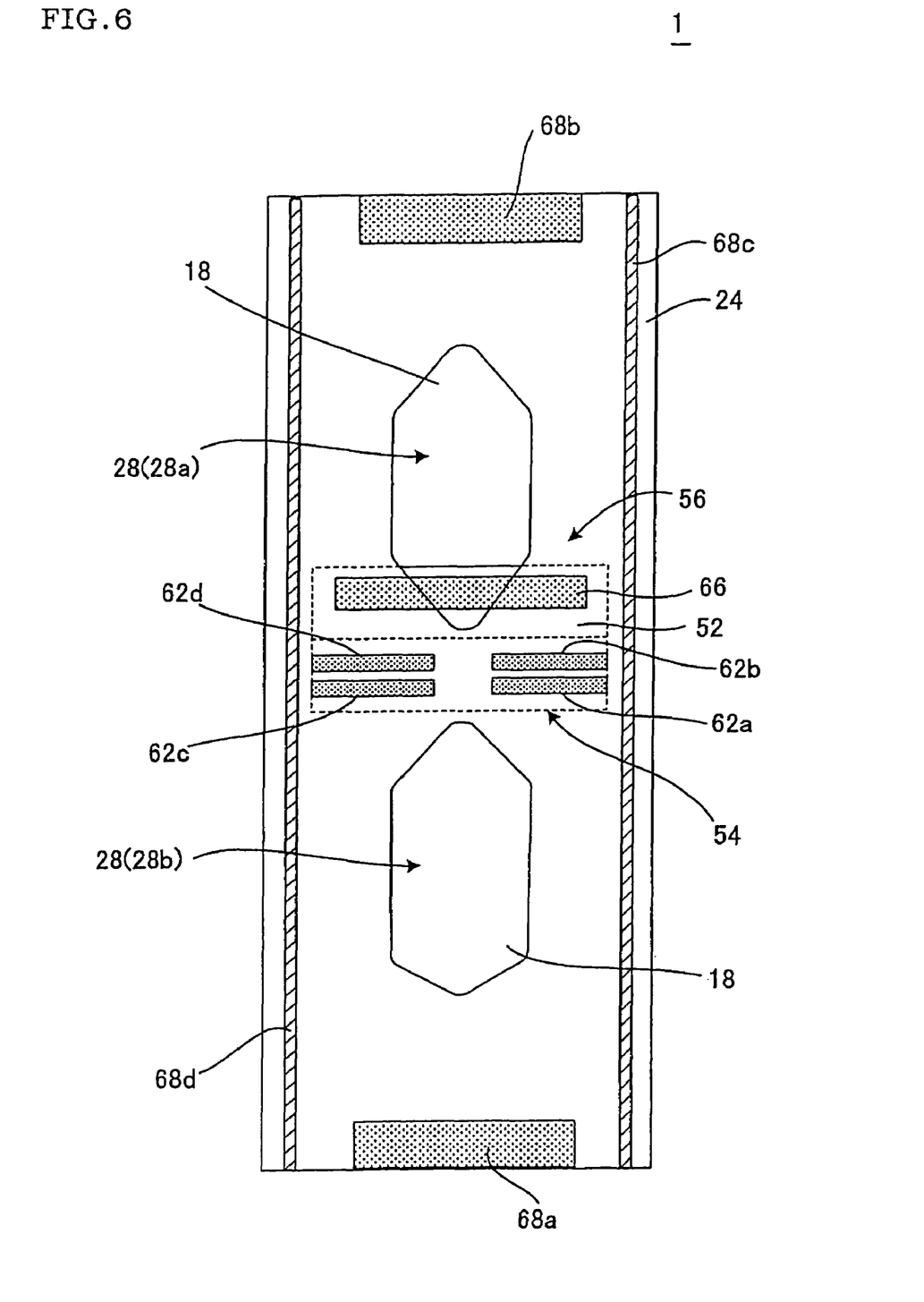
FIG. 6 is a partially enlarged view illustrating the disposable diaper according to the present invention, enlarging the plane of a top sheet part where a breathable water repellant sheet and a skin contact sheet of the disposable diaper shown in FIG. 2 are bonded.

[2-4] The provision of the skin contact sheet and the like to the absorbent member: To the surface of the top sheet 18 which forms the absorbent member 14, each of the front end side, back end side, right side edge side, and left side edge side of the skin contact sheet 24 (i.e., the liner sheet 24b) is pasted and fixed (i.e., joined parts 68a, 68b, 68c, and 68d). Then, the other end 56 of the breathable water repellent sheet 52 is pasted onto the surface of the top sheet 18, joined, and fixed (i.e., a joined part 66). Such fixations can be performed by the bonding methods similar to those used for joining the breathable water repellent sheet to the skin contact sheet. Then, if the breathable water repellent sheet is structured by being folded once or a plurality of times between the bonded parts of the both ends, the standing height of the urine/stool separation wall can be high, and thus preferable. The disposable diaper 1 illustrated in FIG. 4 is an example in which the breathable water repellent sheet 52 is formed in a Z-shape and folded twice. Then, the front end part of the joined part 66 forms a standing line of the urine/stool separation wall 48 at a time of use of the disposable diaper. The disposable diaper 1 illustrated in FIG. 6 is an example in which the front end side, the back end side, the right side edge side and the left side edge side of the skin contact sheet 24 and the other end 56 of the breathable water repellent sheet 52 are pasted with a hot-melt adhesive agent, joined, and fixed to the surface (i.e., the upper surface) of the top sheet 18.

As described above, onto the surface of the top sheet 18, after the front end side, the back end side, the right side edge side and the left side edge side of the skin contact sheet 24 and the other end 56 of the breathable water repellent sheet 52 are pasted, the standing gathers 26a and 26b are pasted so as to sandwich the side edges of the absorbent member 14 and the skin contact sheet 24 (i.e., the liner sheet 24b).

[2-5] The manufacture of the exterior covering member: Two nonwoven fabrics for forming the exterior covering member 16 are first prepared. Then, the waist-surrounding stretchable members 42, the belly-surrounding stretchable members 44, and the leg-surrounding stretchable members 40 are disposed and fixed by adhesion on the upper surface of one of the nonwoven fabrics. Thereafter, the other one of the nonwoven fabrics is layered on and fixed to the upper surface of the one of the nonwoven fabrics. Thereby, the exterior covering member 16 is obtained in which the waist-surrounding stretchable members 42, the belly-surrounding stretchable members 44, and the leg-surrounding stretchable members 40 are interposed between the two nonwoven fabrics.

[2-6] The manufacture of the disposable diaper: The absorbent member 14 is disposed at and fixed to the proximity of the crotch part of the exterior covering member 16. Then, the exterior covering member 16 is folded in half such that the front body part 2 and the back body part 6 are aligned with each other, with the absorbent member 14 on the inside of the folded exterior covering member 16. Thereafter, the front body part 2 and the back body part 6 are joined by such a method as heat-sealing, and the joining parts 8 are formed. Thereby, the disposable diaper 1 illustrated in FIGS. 1 to 4 is manufactured.

The above-described sequence of processes can be continuously performed by a mechanical method. For example, with a method or apparatus for continuously sending out a long sheet material or a long stretching material by a roller, for example, the continuous manufacture of the disposable diaper can be performed. This contributes to the improvement of the productivity.

[3] The scope of application of the present invention: The scope of application of the disposable diaper according to the present invention is not limited to the above-described two-piece-type and pants-type diaper, but the present invention is also applicable to a one-piece-type and pants-type diaper and a tape-type diaper, for example. That is, these diapers can also have the effects of the disposable diaper according to the present invention, if the skin contact sheet is disposed to a part higher than the surface of the top sheet and is provided with the urine/stool separation wall which is made of a breathable water repellent sheet.

The "one-piece-type diaper" refers to a type of diaper which includes a top sheet, a back sheet, and an absorber, similarly to the two-piece-type diaper, but in which the absorber having the absorbing and retaining function is interposed (i.e., embedded) between the top sheet and the back sheet and is integrated with the top sheet and/or the back sheet having the fitting function.

The "tape-type diaper" refers to a disposable diaper which includes a top sheet, a back sheet, an absorber interposed between at least parts of the two sheets, and tape fasteners for fitting the diaper, and in which a front body part and a back body part can be fixed to each other by the tape fasteners. The "tape-type diaper" also includes the "one-piece-type" and the "two-piece-type," and the disposable diaper according to the present invention is applicable to either type of the tape-type diaper.

The disposable diaper according to the present invention can be preferably used as the diaper for an infant or an adult such as an elder or disabled person who needs nursing care. Further, in the disposable diaper according to the present invention, mixture of urine and stool can be effectively prevented, and occurrence of diaper rash due to the mixture of the urine and stool can be effectively reduced. Accordingly, the disposable diaper according to the present invention can be preferably used particularly as the disposable diaper for an infant who has a sensitive skin and thus frequently has skin trouble.

What is claimed is:

1. A disposable diaper comprising:
   an absorber;
   a top sheet disposed to cover an upper surface of the absorber, the top sheet being at least partially formed of a liquid permeable material;
   a back sheet, formed of a liquid impermeable material, disposed to cover a lower surface of the absorber;
   a skin contact sheet laminated above the top sheet and having both a stool passing opening, capable of passing a stool therethrough, and a urine passing opening formed therein; and
   a urine/stool separation wall, formed of a discrete breathable water repellent sheet, located within a space defined between the skin contact sheet and the top sheet so that the space is separated into a front body part side space and a back body part side space;
   wherein when the diaper is in a fully relaxed state, a portion of the surface of the top sheet located directly under the stool passing opening is at least partially covered by and in direct contact with a portion of the discrete breathable water repellent sheet defining the urine/stool separation wall to prevents urine present in the absorber from leaking out of the absorber, passing through the top sheet into the back body part side space and contacting stool present therein, and wherein another portion of the surface of the top sheet located directly under the urine passing opening is not covered by any portion of the discrete breathable water repellent sheet of the urine/stool separation wall.

2. The disposable diaper according to claim 1, wherein one end of the breathable water repellent sheet of the urine/stool separation wall is joined to the skin contact sheet and the other end of the breathable water repellent sheet of the urine/stool separation wall extends downwardly toward a surface of the top sheet to form the urine/stool separation wall.

3. The disposable diaper according to claim 2, wherein the other end of the breathable water repellent sheet of the urine/stool separation wall is joined to the top sheet.

4. The disposable diaper according to claim 3, wherein the urine/stool separation wall is interposed between the stool passing opening and the urine passing opening formed in the skin contact sheet so that the back body part side space communicates with the stool passing opening and the front body part side space communicates with the urine passing opening.

5. The disposable diaper according to claim 2, wherein the urine/stool separation wall is interposed between the stool passing opening and the urine passing opening formed in the skin contact sheet so that the back body part side space communicates with the stool passing opening and the front body part side space communicates with the urine passing opening.

6. The disposable diaper according to claim 1, wherein the urine/stool separation wall is interposed between the stool passing opening and the urine passing opening formed in the skin contact sheet so that the back body part side space communicates with the stool passing opening and the front body part side space communicates with the urine passing opening.

7. The disposable diaper according to claim 1, wherein no more than 50% of the portion of the surface of the top sheet located directly under the stool passing opening is covered with the breathable water repellant sheet of the urine/stool separation wall.

8. The disposable diaper according to claim 1, wherein the portion of the surface of the top sheet located directly under the stool passing opening is fully covered with the breathable water repellant sheet of the urine/stool separation wall.

* * * * *